US008616215B2

(12) United States Patent
Khajavi et al.

(10) Patent No.: US 8,616,215 B2
(45) Date of Patent: Dec. 31, 2013

(54) SYSTEM AND METHOD FOR PREVENTING WRONG-SITE SURGERIES

(75) Inventors: Kaveh Khajavi, Atlanta, GA (US); James D. Griffin, Conyers, GA (US)

(73) Assignee: StartBox, LLC, Decatur, GA (US)

( * ) Notice: Subject to any disclaimer, the term of this patent is extended or adjusted under 35 U.S.C. 154(b) by 400 days.

(21) Appl. No.: 11/270,686

(22) Filed: Nov. 9, 2005

(65) Prior Publication Data

US 2006/0096877 A1     May 11, 2006

Related U.S. Application Data

(60) Provisional application No. 60/626,240, filed on Nov. 9, 2004.

(51) Int. Cl.
| A61F 13/06 | (2006.01) |
| B65D 59/00 | (2006.01) |
| A61B 17/06 | (2006.01) |
| B65D 83/10 | (2006.01) |

(52) U.S. Cl.
USPC ............ 128/898; 206/570; 206/438; 206/807

(58) Field of Classification Search
USPC ......... 206/370, 364, 365, 366, 438, 570, 571, 206/807, 459.5; 40/312; 604/189; 128/898
See application file for complete search history.

(56) References Cited

U.S. PATENT DOCUMENTS

| 1,625,035 | A |   | 4/1927  | Lilly   |         |
|-----------|---|---|---------|---------|---------|
| 3,391,694 | A | * | 7/1968  | Spaeth  | 604/189 |
| 3,497,982 | A | * | 3/1970  | Schulz  | 40/312  |
| 3,517,636 | A |   | 6/1970  | Colon-Morales |   |
| 3,698,383 | A | * | 10/1972 | Baucom  | 600/584 |
| 3,727,749 | A |   | 4/1973  | Martin  |         |
| 4,243,140 | A | * | 1/1981  | Thrun   | 206/380 |
| 4,373,629 | A |   | 2/1983  | Ulin et al. |     |
| 4,476,381 | A | * | 10/1984 | Rubin   | 235/375 |

(Continued)

FOREIGN PATENT DOCUMENTS

| WO | WO 94/24021 | 10/1994 |
| WO | WO 96/31414 | 10/1996 |

OTHER PUBLICATIONS

Arnold A. Zeal, MD.; Error Results in Doctor's Paradigm Shift; vol. 14, No. 4, AANS Bulletin 27; 2 pgs.

(Continued)

*Primary Examiner* — J. Gregory Pickett
*Assistant Examiner* — Kaushikkumar Desai
(74) *Attorney, Agent, or Firm* — McHale & Slavin, P.A.

(57) ABSTRACT

A container holds at least one surgical implement, has a lock mechanism, and has a signature label that impedes access to the surgical implement until the correct surgical site is confirmed. A method of using the container includes the steps of confirming the correct surgical site, signing the label and removing it from the container, placing the label in the medical record, unlocking the container, removing the implement, and beginning the surgery, wherein the surgical team is forced to pause to confirm the correct surgical site before starting the surgery. Preferably, the container top may be removed and placed between the surgeon and surgical technician to define a no-hands "neutral zone" to avoid being stuck by the sharps. Also, the container preferably includes compartments for storing used sharps and/or a local anesthetic-loaded syringe, and the top may be replaced and secured for safely disposing of the sharps after the surgery.

22 Claims, 8 Drawing Sheets

(56) References Cited

U.S. PATENT DOCUMENTS

| | | | | |
|---|---|---|---|---|
| 4,620,644 A * | 11/1986 | Miller | | 220/826 |
| 4,736,844 A | 4/1988 | Scott et al. | | |
| 4,848,587 A * | 7/1989 | Nipp | | 206/571 |
| 4,944,603 A * | 7/1990 | Cornish et al. | | 383/5 |
| 4,979,616 A * | 12/1990 | Clanton | | 206/364 |
| 5,024,326 A * | 6/1991 | Sandel et al. | | 206/366 |
| 5,031,768 A * | 7/1991 | Fischer | | 206/370 |
| 5,067,612 A * | 11/1991 | Tsuchiya et al. | | 206/497 |
| 5,167,193 A | 12/1992 | Withers et al. | | |
| 5,181,609 A | 1/1993 | Spielmann et al. | | |
| 5,193,678 A | 3/1993 | Janocik et al. | | |
| 5,195,538 A | 3/1993 | Eldridge, Jr. et al. | | |
| 5,225,162 A * | 7/1993 | Scoville | | 422/401 |
| 5,293,990 A * | 3/1994 | Masakayan | | 206/1.5 |
| 5,318,543 A * | 6/1994 | Ross et al. | | 604/170.01 |
| 5,338,123 A * | 8/1994 | Obersteller et al. | | 401/34 |
| 5,339,955 A * | 8/1994 | Horan et al. | | 206/370 |
| 5,356,006 A * | 10/1994 | Alpern et al. | | 206/363 |
| 5,381,487 A * | 1/1995 | Shamos | | 382/115 |
| 5,394,982 A | 3/1995 | Sawaya | | |
| D374,282 S * | 10/1996 | Hoftman | | D24/130 |
| 5,566,828 A | 10/1996 | Claes et al. | | |
| 5,829,788 A * | 11/1998 | Jackson | | 283/81 |
| 5,938,063 A | 8/1999 | Hoftman | | |
| 5,976,014 A * | 11/1999 | Petrick et al. | | 462/3 |
| 6,056,737 A * | 5/2000 | Rosen | | 606/1 |
| 6,158,437 A * | 12/2000 | Vagley | | 128/898 |
| 6,247,592 B1 | 6/2001 | Racicot et al. | | |
| 6,343,695 B1 * | 2/2002 | Petrick et al. | | 206/534 |
| 6,364,096 B1 * | 4/2002 | De Baets et al. | | 206/1.5 |
| 6,685,017 B2 | 2/2004 | Erickson | | |
| 6,923,319 B1 | 8/2005 | Erickson et al. | | |
| 7,032,752 B2 * | 4/2006 | Krackow | | 206/438 |
| 7,635,348 B2 * | 12/2009 | Raven et al. | | 604/111 |
| 2002/0014029 A1 * | 2/2002 | Copelan | | 40/638 |
| 2002/0179094 A1 * | 12/2002 | Perlow | | 128/897 |
| 2003/0111361 A1 | 6/2003 | Fischer et al. | | |
| 2003/0187458 A1 * | 10/2003 | Carlson, II | | 606/116 |
| 2004/0031708 A1 * | 2/2004 | Spagna | | 206/308.2 |
| 2004/0033327 A1 * | 2/2004 | Marks et al. | | 428/42.3 |
| 2004/0056478 A1 | 3/2004 | Bruce | | |
| 2004/0069667 A1 * | 4/2004 | Tomellini et al. | | 206/364 |
| 2004/0116907 A1 | 6/2004 | Tartaglia | | |
| 2004/0118410 A1 * | 6/2004 | Griesbach et al. | | 128/852 |
| 2004/0128892 A1 * | 7/2004 | Valenti, Jr. | | 40/633 |
| 2004/0163982 A1 | 8/2004 | Wilkinson et al. | | |
| 2004/0261644 A1 * | 12/2004 | Stewart et al. | | 101/483 |
| 2005/0038407 A1 * | 2/2005 | Sumka | | 604/500 |
| 2005/0045503 A1 * | 3/2005 | Wong et al. | | 206/308.2 |
| 2006/0042977 A1 | 3/2006 | Sandel | | |
| 2006/0096877 A1 * | 5/2006 | Khajavi et al. | | 206/363 |
| 2006/0124493 A1 * | 6/2006 | Krackow | | 206/438 |

OTHER PUBLICATIONS

Joint Commission on Accreditation of Healthcare Organizations. Sentinel Events Alert; A Follow-Up Review of Wrong Site Surgery; Dec. 5, 2001; 4 pgs; Issue 24; www.jcaho.org.

David A. Wong, MD, MSc, FRCS (C) and Stanley A. Herring, MD; North American Spine Society; NASS Endorses JCAHO Universal Protocol; Mar./Apr. 2004; 3 pgs.

Gerald B. Healy, MD, FACS, and Jack Barker, PhD, and Capt. Gregory Madonna; Error Reduction Through Team Leadership: Applying Aviation's CRM Model in The OR; vol. 91, No. 2, Bulletin of the American College of Surgeons; Feb. 2006; 6 pgs.

Alan Cash, R.N., J.D.; Nursing Risk Management 2003 Department of Legal Medicine; Wrong Site Surgery; 15 pgs.

American Academy of Orthopaedic Surgeons; Wrong Site Surgery; 1998; 2 pgs; Rosemont, IL.

Sentinel Event Statistics; Dec. 31, 2005; 1 pg.

Joint Commission on Accreditation of Healthcare Organizations. Sentinel Events: Approaches to Error Reduction and Prevention; vol. 24, No. 4; 13 pgs.

Sandel Medical Industries, LLC; Time Out Safety Kit; May 12, 2006; 3 pgs; www.sandelmedical.com/productdetail.aspx?id=26.

David A. Wong, MD. MSc, FRCS(C) and Stanley A. Herring, MD; Special Feature-NASS Endorses JCAHO Universal Protocol, Guidelines for Implementing the Universal Protocol for Preventing Wrong Site, Wrong Procedure and Wrong Person Surgery; Article; Date on Article Mar./Apr. 2004; 3 pages; Publisher/North American Spine Society.

Eric G. Meinberg and Peter J. Stern; Incidence of Wrong-Site Surgery Among Hand Surgeons; The Journal of Bone & Joint Surgery JBJS; Date of Article Feb. 12, 2009; 6 pages; Publisher/The Journal of Bone and Joint Surgery; Needham, MA.

The Joint Commission; Sentinel Event Statistics—Dec. 31, 2008; Web Article—www.jointcommission.org/SentinelEvents/Statistics/; Date printed, Feb. 12, 2009; 3 pages; Publisher/The Joint Commission.

The Joint Commission; Sentinel Event Alert—Lessons Learned: Wrong Site Surgery; Web Article—www.jointcommission.org/SentinelEvents/SentinelEventAlert/; Date printed, Feb. 26, 2009; 1 page; Publisher/The Joint Commission.

Steven Reinberg; Surgeon's Checklist Saves Lives; Web Article—www.washingtonpost.com/wp-dyn/content/article/2009/01/14...; Date of Article, Jan. 14, 2009; Date printed, Feb. 18, 2009; 2 pages; Publisher/Scout News LLC.

Steve Phurrough, MD, MPA, Marcel E. Salive, MD, MPH, Madeline Ulrich, MD, MS, Sarah McClain, MHS; Decision Memo for Surgery on the Wrong Body Part (CAG-00402N), Subject: Coverage Decision Memorandum for Surgical or Other Invasive Procedure Performed on the Wrong Body Part; Memorandum; Date of Memorandum, Jan. 15, 2009, Dated printed, Jan. 23, 2009; 9 pages.

Steve Phurrough, MD, MPA, Marcel E. Salive, MD, MPH, Madeline Ulrich, MD, MS, Sarah McClain, MHS; Decision Memo for Surgery on the Wrong Patient (CAG-00403N), Subject: Coverage Decision Memorandum for a Surgical or Other Invasive Procedure Performed on the Wrong Patient; Memorandum; Date of Memorandum, Jan. 15, 2009; Dated printed, Jan. 23, 2009; 8 pages.

Steve Phurrough, MD, MPA, Marcel E. Salive, MD, MPH, Madeline Ulrich, MD, MS, Sarah McClain, MHS; Decision Memo for Wrong Surgery Performed on a Patient (CAG-00401N), Subject: Coverage Decision Memorandum for Wrong Surgical or Other Invasive Procedure Performed on a Patient; Memorandum; Date of Memorandum, Jan. 15, 2009; Dated printed, Jan. 23, 2009; 9 pages.

Goldie Blumenstyk; A System to Prevent 'Wrong-Site Surgery'; Article; Date of Article, Feb. 17, 2006; 2 pages; vol. 52, Issue 24, p. A35; Publisher/Chronicle.com.

Mary R. Kwaan, MD, MPH, David M. Studdert, LLB, ScD; Michael J. Zinner, MD, Atul D. Gawande, MD, MPH; Incidence, Pattersn, and Prevention of Wrong-Site Surgery; Article; Date of Article, Jan. 24, 2007; 6 pages; Arch Surg/vol. 141; Publisher/American Medial Association.

John R. Clarke, MD, Janet Johnston, MSN, MD, Edward D. Finley, BS, Desiree Lie, MD, MSEd; Annals of Surgery Getting Surgery Right CME; Article; Release date Nov. 16, 2007; 23 pages; Medscape, LLC.

Henry R. Cowell, MD, PhD.; Wrong-Site Surgery; Editorial; Date of editorial, Apr. 1998; 1 page; vol. 80-A, No. 4; Publisher/The Journal of Bone and Joint Surgery, Inc.

Samuel C. Seiden, MD, Paul Barach, MD, MPH; Wrong-Side/Wrong-Site, Wrong-Procedure, and Wrong-Patient Adverse Events; Web Article—www.archsurg.ama-assn.org/cgi/content/full/141/9/931#REF-SOA6...; Date of web article, Sep. 2006; Date printed, Feb. 12, 2009; 15 pages; vol. 141, No. 9; Publisher/American Medical Association.

Robert Davis, USA Today; Wrong-Site Surgeries on the Rise; Web Article—www.usatoday.com/news/health/206-04-17-wrong-surgery_x.htm; Date of Article, Apr. 17, 2006; Date printed, Feb. 7, 2009; 2 pages; Publisher/USA Today.

* cited by examiner

REMOVE LABEL A TO ACCESS SURGICAL PEN.
SIGN AND REMOVE LABEL B TO OPEN SURGICAL TRAY.

CONFIRMATION & SIGNATURES/LABEL B

PATIENT NAME: ______________________________________

OPERATIVE SITE/SURGICAL PROCEDURE: ___________________

NECESSARY IMPLANTS AND/OR INSTRUMENTS PRESENT:   Y   N

SIGNATURES:
    SURGICAL TECH: ____________________________________
    NURSE: ____________________________________________

I/WE HAVE REVIEWED THE PERTINENT CLINICAL RECORDS, INCLUDING RADIOGRAPHS, AND CONFIRMED THE ABOVE TO THE CORRECT.

SURGEON SIGNATURE: _________________________________

PEEL

SURGICAL PEN/LABEL A     PEEL

SYSTEM AND METHOD FOR PREVENTING WRONG-SITE SURGERIES

CROSS-REFERENCE TO RELATED APPLICATION

This application claims the priority benefit of U.S. Provisional Patent Application Ser. No. 60/626,240, filed Nov. 9, 2004, the entire scope and content of which is hereby incorporated herein by reference.

TECHNICAL FIELD

The present invention relates generally to surgical devices and procedures and, in particular, to surgical devices and procedures for preventing wrong-site surgeries.

BACKGROUND OF THE INVENTION

A great deal of attention has recently been given to the unacceptable rate of avoidable patient injuries, or so-called medical mistakes, in the United States. Estimates of the number of medical mistakes per year in the United States is difficult to ascertain, but a recent publication, *To Err is Human*, by Dr. Lucian Leape, suggests that the avoidable death rate for medical mistakes at between 48,000 and 96,000 patients per year.

As defined by the Joint Commission on Accreditation of Healthcare Organizations (JCAHO), wrong-site surgery includes wrong side or site of the body, wrong procedure, and wrong-patient surgeries.

Prevalence of Wrong-Site Surgery

From January 1995 to March 2001, JCAHO reviewed voluntary reports of 1152 "sentinel events." Wrong-site surgery accounted for 114 cases (9.9%) and included procedures in neurosurgery, urology, orthopedics, and vascular surgery. Despite the high profile of JCAHO's Sentinel Event Policy, under-reporting by healthcare organizations likely affects these statistics. Only 66% of the 1152 total events were "self-reported" by the institutions involved, the balance coming from patient complaints or media stories[1]. Using a mandatory reporting system, the New York State Department of Health received 46 reports of wrong-site surgery from Apr. 1, 1998 through Mar. 31, 2000, compared with 114 cases JCAHO received nationally over a period 3 times longer. This suggests that voluntary incident reporting may grossly underestimate the true incidence of wrong-site surgery by a factor of 20 or more.

The Physician's Insurance Association of America (PIAA) reviewed the claims data from 22 malpractice carriers representing 110,000 physicians from 1985 to 1995. There were 331 cases of wrong-site surgery. The complete PIAA database documents almost 1000 closed malpractice claims involving wrong-site surgery. However, this figure also likely underestimates the prevalence of wrong-site surgery. Since most wrong-site surgeries involve relatively minor procedures (arthroscopy, rather than limb amputations or major neurosurgical procedures), sequelae are minimal and may not result in a claim. Consequently, estimates of the incidence of wrong-site surgery derived from litigation data likely underestimate the true prevalence of this problem, as do estimates based on incident reports.

Factors Identified as Contributing to Wrong-Site Surgery

Several factors have been identified that may contribute to an increased risk of wrong-site surgery. These risk factors include:

More than one surgeon involved in the case, either because multiple procedures were contemplated or because the care of the patient was transferred to another surgeon;

Multiple procedures were conducted on the same patient during a single trip to the operating room, especially when the procedures were on different sides of the patient;

Unusual time pressures, related to an unusual start time or pressure to speed up the preoperative procedures; and Unusual patient characteristics such as physical deformity or massive obesity that might alter the usual process for equipment set-up or positioning of the patient.

The root causes identified by hospitals were most often related to communication, preoperative assessment of the patient, and the procedures used to verify the operative site. Communication issues fall into two major categories:

Failure to engage the patient (or family, when appropriate) in the process of identifying the correct surgical site, either during the informed consent process or by the physical act of marking the intended surgical site; and Incomplete or inaccurate communication among members of the surgical team, often through exclusion of certain members of the team (e.g., surgical technicians) from participation in the site verification process, or through reliance solely on the surgeon for determining the correct operative site.

The completeness of the preoperative assessment of the patient was a frequent contributing factor, often through failure to review the medical record or imaging studies in the immediate preoperative period. The procedures for verifying the correct operative site were found to be flawed in many cases due to:

No formal procedure;

No final check in the operating room;

The absence of any oral communication in the verification procedure;

All relevant information sources not available in the operating room;

No checklist to ensure all relevant information sources were checked;

Some members of the surgical team were excluded from the verification process and felt they were not permitted to point out a possible error; and Total reliance on the surgeon for verifying the surgical site.

JCAHO Strategies for Reducing Wrong-Site Surgery

The Joint Commission offers the following possible strategies for reducing the risk of wrong-site surgery:

Clearly mark the operative site and involve the patient in the marking process to enhance the reliability of the process;

Require an oral verification of the correct site in the operating room by each member of the surgical team;

Develop a verification checklist that includes all documents referencing the intended operative procedure and site, including the medical record, X-rays and other imaging studies and their direct observation of the marked operative site on the patient;

Personal involvement of the surgeon in obtaining informed consent;

Ensure through ongoing monitoring that verification procedures are followed for high-risk procedures; and "Time out" immediately before starting the procedure.

(Source: Joint Commission on Accreditation of Healthcare Organizations. Sentinel Event Alert, issue six, Aug. 28, 1998.)

Despite the implementation of strategies to prevent wrong patient, wrong site, wrong side surgery, regrettably this seemingly most preventable of complications still occurs. (The aforementioned statistics do not address the number of times in which implants or instrumentation is going to be placed as a part of the procedure, and are not available when the surgeon is ready for them. In these instances, the surgeon must either change plans, or wait while the surgical team attempts to locate the appropriate implants or instrumentation, sometimes located at another hospital.) The fraudulent assumption of a medical professional's infallibility, coupled with organized medicine's focus on the individual's medical mistakes rather than a systems approach, have contributed to this problem. In an attempt to improve patient safety, "[e]ffective Jul. 1, 2004, compliance with the *Universal Protocol for Preventing Wrong Site, Wrong Procedure, Wrong Person Surgery* will be required of all Joint Commission accredited organizations." As a part of the universal protocol, a "pause" or "time out" is required. This serves as a final verification of: (1) the correct patient; (2) the correct procedure, site and side (3); and as applicable, (4) the availability of implants or instrumentation, prior to making incision. This is a time when all members of the surgical team are supposed to pause to review the case, and agree that the correct procedure is being done in the correct patient, at the correct site, and on the correct side. In theory, this would ensure that any errors that had been made could be detected prior to incision. In reality, the "time out" seldom occurs, and when it does, not in any uniform or regular manner. The universal protocol does not specify a particular time for the pause to occur, and it does not specify a protocol as to what should happen during the pause, that is to say, what information should be communicated by whom, and to whom.

Accordingly, it can be seen that a need exists for improvements to surgical procedures and devices to prevent or at least reduce wrong-site surgeries. It is to the provision of meeting these and other needs that the present invention is primarily directed.

SUMMARY OF THE INVENTION

Generally described, the present invention provides a system and method for preventing wrong-site surgeries by imposing a pause just before the surgery starts, during which time the surgical team conducts a pre-operative assessment to confirm that correct site of the surgery about to be performed. By imposing the pre-operative assessment, the surgical team gets one last chance to catch any avoidable mistake that would otherwise lead to a wrong-site surgery.

In a first example embodiment of the present invention, the system includes a container that holds one or more surgical implements, a lock mechanism for securing the container closed, and a removable confirmation label that blocks or at least impedes access to the lock mechanism. The surgeon cannot readily open the container to get the surgical implements until the correct surgical site has been confirmed and the label has been removed. The surgical implements include one or more scalpels or other blades, a syringe loaded with a local anesthetic, a needle, a scope, and/or other surgical implements needed at the outset of the surgery. The label includes, for example, a checklist for confirming surgery-related information and one or more fields for signatures.

In one aspect of the invention, the lock mechanism includes a lock member that fits through two openings in the container that align when the container is closed. Preferably, the container includes a bottom and a top that slides off the bottom, with one lock opening being through the top, and the other lock opening formed into an internal divider wall that also defines compartments for the surgical implements.

In another aspect of the invention, the container bottom has one or more dedicated compartments for surgical needles. In use, the bottom may be positioned beside a surgical team member for storing surgical needles after they have been used in the surgery. Then at the conclusion of the surgery, the container may be closed and the surgical sharps all safely disposed of at once.

In yet another aspect of the invention, the container top can be removed from the bottom and positioned between the surgeon and a surgical team member to define a neutral zone where hands do not meet. With the neutral zone clearly defined, the incidence of stickings when passing the surgical sharps back and forth is reduced.

In use, the system forces a surgery team pause prior to initiating the surgery, after the patient is draped and the surgeon and surgical technician are both sterilely gowned, when all members of the surgical team pause to make sure that they have the correct patient, the correct operation is being performed, on the correct site and side, and all necessary surgical instrumentation or implants are physically available. Once that information is confirmed, which might require the surgeon to review the medical record or the imaging studies, the surgeon removes a dual-tipped pen from the top of the container and uses the ink side to sign the label on the box. Then the label is then removed and placed in the medical record, and the surgeon now has access to the lock to open the container and remove the surgical implement(s). The surgical marking pen side of the pen can be used to mark the incision. The container top is then turned upside down and serves as the surgical neutral zone, which defines a hands-free "neutral zone" where sharp instruments can be traded between the surgeon and surgical technician without the actual passing of sharp instruments from hand to hand. In addition, the container may also have pre-loaded local anesthetic with a needle and syringe, to further expedite the starting of the operation. Furthermore, compartments in the container will have foam padded areas, with printed numbers, for the counting and storage of suture needles, as well as other sharps, and at the end of the case the container can be reclosed securely, with all the sharps in the container accounted for, and safely disposed of as one unit.

In a second example embodiment, the container bottom has four compartments with a shorter syringe compartment. In a third example embodiment, the label is attached to the top and bottom of the container to lock it closed, so that the label doubles as the lock. In a fourth example embodiment, the lock member is provided by a tie member that fits through aligned openings formed by two external tabs on the container, and the label covers the lock member. In a fifth example embodiment, the lock member is provided by a wrapper that encloses the container, and the label is removably attached to the wrapper or to a pull tab for opening the wrapper. And in still other embodiments, the container does not include a lock mechanism, or it does include a lock mechanism and the label does not cover it, but the label impedes access to opening the container by being prominently positioned so that it is hard not to notice it, which prompts a pause for the surgical team to conduct the pre-operative assessment to confirm the correct site of the surgery.

The method of preventing wrong-site surgery comprises the steps of providing a container that holds a surgical implement and has a label for confirming surgery-related information, with the label removably attached to the container; using the label to conduct a pre-operative assessment confirming a correct surgical site; removing the label from the container; opening the container and removing the surgical implement; and using the surgical implement at the outset of the surgery.

In this way, the pre-operative assessment confirming that the correct surgical site has been identified is done before making an incision and starting the surgery. Preferably, the container is provided with a lock mechanism securing it closed, and the label is positioned blocking access to the lock mechanism so that the label must be removed to open the container.

In one aspect of the method, the container includes a top that is removed to open the container. The method further includes the steps of positioning the removed container top between a surgeon and a surgical team member to define a neutral zone where hands do not meet; and exchanging surgical sharps between the surgeon and the surgical team member without sticking each other. The exchanging is done by the surgeon placing the surgical sharps into the container top and the surgical team member then picking them up, and vice versa.

In another aspect of the method, the container includes a bottom with at least one compartment that holds the surgical implement and with one or more additional compartments for surgical needles, and positioning the removed container bottom beside a surgical team member. The method further includes the steps of, after the surgical needles have been used in the surgery, storing the used surgical needles in the dedicated compartments in the container bottom. In addition, the method includes replacing the top on the container to close the container at the conclusion of the surgery; and disposing of the container with the used sharps safely inside.

The specific techniques and structures employed by the invention to improve over the drawbacks of the prior devices and accomplish the advantages described herein will become apparent from the following detailed description of the example embodiments of the invention and the appended drawings and claims.

DETAILED DESCRIPTION OF EXAMPLE EMBODIMENTS

Referring to the drawing figures, the present invention includes a surgical system and a method of using the surgical system to impose a preoperative assessment to prevent wrong-site surgeries. The system includes a container that holds one or more surgical implements needed for the surgery, a lock mechanism that secures the container in a closed position, and a confirmation and/or signature label in a position that prevents or at least impedes access to the lock. In this way, the surgical team is forced to pause to deal with the label in order to access the surgical implements needed to start the surgery.

Referring to FIGS. 1-11, where is illustrated a surgical system 10 according to a first example embodiment of the present invention. FIGS. 1-4 show the surgical container 12, the lock mechanism 14, and the confirmation and signature label 16 of the surgical system 10. The container 12 has a bottom 18 and a top 20 that that can be positioned in the closed position of FIG. 1 or the opened position of FIG. 4. In the depicted embodiment, the top 18 and the bottom 20 slide relative to each other to open and close the container 12. For example, the container 12 may include a lip-and-groove arrangement 22 to permit the top 20 to be slid off of the bottom 18. In addition, the container 12 may include detents or other structures for snapping closed the top 20 and bottom 18 so that the container cannot freely slide open when it is unlocked. In alternative embodiments, the container has hinge for a pivotal opening motion, preferably with the hinge permitting the top to be separated from the bottom. The size of the container 12 is selected based primarily on the intended contents and may be customized for different types of surgeries and/or different surgeons. In general, though, the container 12 is not too large to be obtrusive or too small to escape notice. In a typical commercial embodiment, the container 12 is about 1-2 inches high, about 4-6 inches wide, and about 8-10 inches long. In addition, the container 12 is preferably generally rectangular with scalloped top edges for ease of gripping, and is preferably made of a plastic material, though other materials may be suitably employed.

Preferably, the bottom surface of the bottom 18 and the top surface of the top 20 are provided with gripping features so that they will not slip on a substantially horizontal surface they are resting upon. For example, the gripping features may include a layer 13 of frictional material such as rubber or soft plastic inlayed or applied onto to the top surface (or a portion thereof of the top 20, and an adhesive-backed pad 15 of frictional material such as rubber or soft plastic attached to the bottom surface of the bottom 18. In this way, the bottom 18 and the inverted top 20 are held in place during use, as described in detail below.

Figure 1:
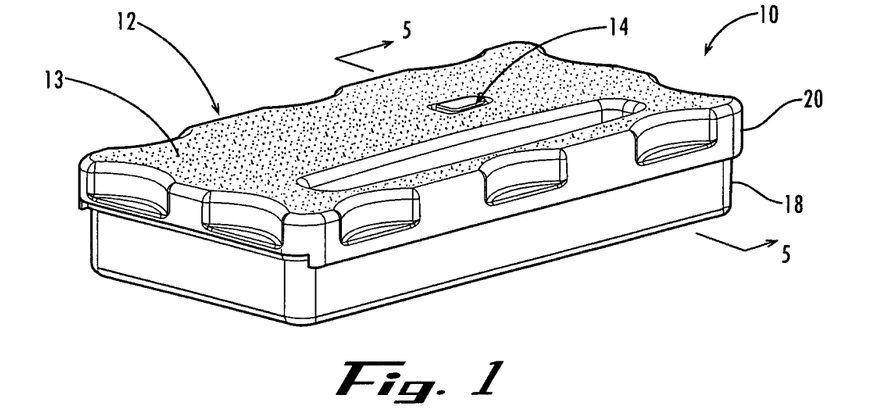
FIG. 1 is a perspective view of a container for surgical sharps according to a first example embodiment of the invention, showing the container in a closed and locked position.
Figure 2:
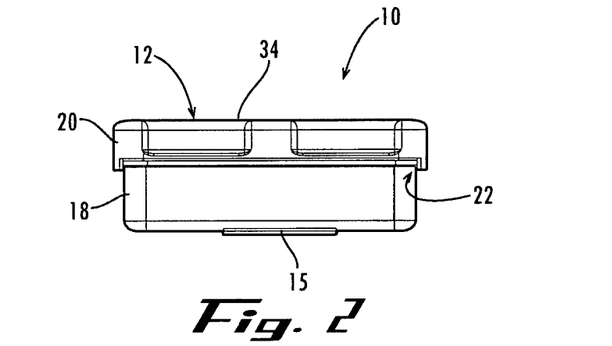
FIG. 2 is a left side view of the container of FIG. 1.
Figure 3:
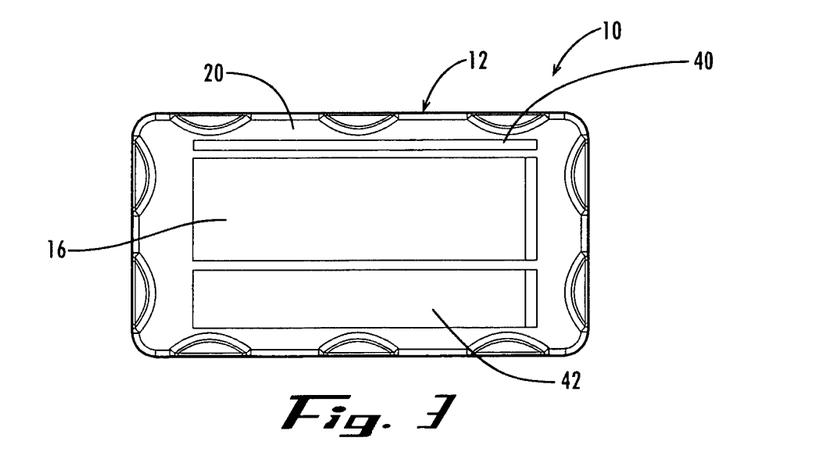
FIG. 3 is a plan view of the container of FIG. 1, showing labels on the container, including a confirmation/signature label covering a lock member so that the container cannot be unlocked and opened until the label is removed.
Figure 4:
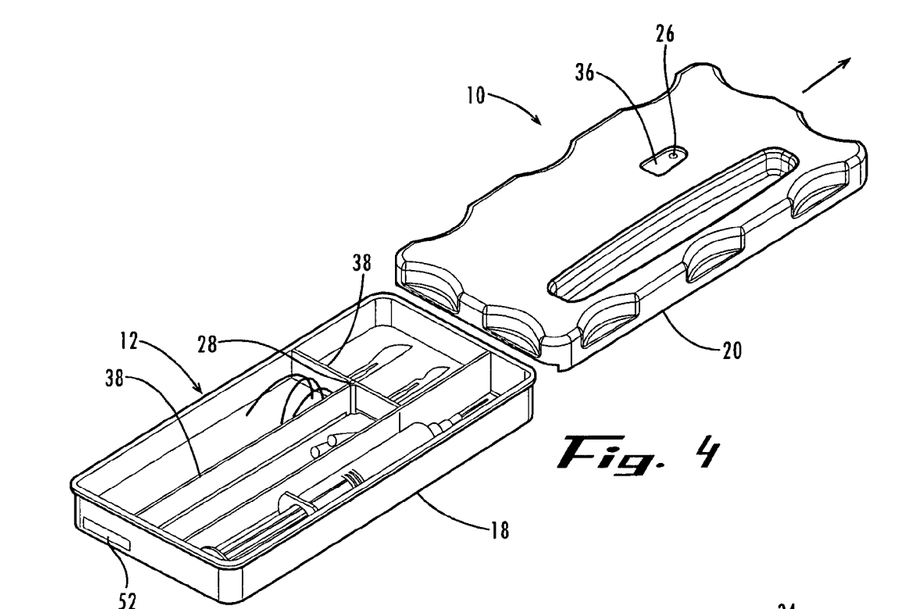
FIG. 4 is a perspective view of the container of FIG. 1 in an unlocked and open position.
Figure 5:
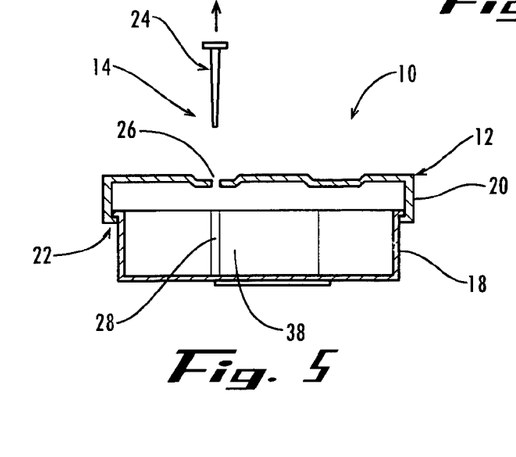
FIG. 5 is a cross section view of the container of FIG. 1 taken at line 5-5, showing a lock member being removed from aligned lock openings to unlock the container.
Figure 6:
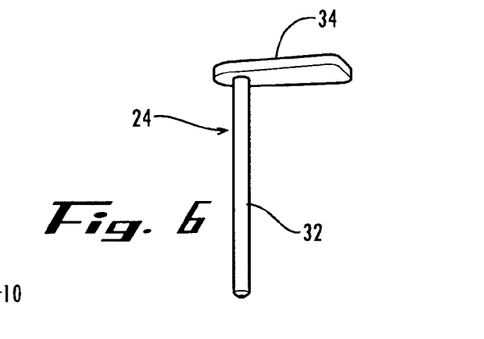
FIG. 6 is a perspective view of the lock member of FIG. 5.

Referring additionally to FIGS. 5 and 6, the lock mechanism 14 secures the container 12 in the closed position. The lock mechanism 14 preferably includes a lock member that is received in locking engagement through two aligned lock openings in the top and bottom of the container. For example, in the depicted embodiment the lock member 24 linearly slides into a first lock opening 26 in the top 20 and a second lock opening 28 in the bottom 18 when the container 12 is in the closed position. The lock member 24 preferably includes a lock pin 32 that is received in the aligned openings 28 and 30 and a tab 34 for ease of grasping by hand. The top 20 may have a recess 36 configured to at least partially receive the tab 34 to provide a low profile, with the first lock opening 26 positioned within the recess. The second lock opening 28 is preferably formed into one or more divider walls 38 that define compartments in the bottom 18, so that the opening is out of the way and so a separate upstanding structure is not required for defining the opening. And the lock member 24 can be made of a plastic, metal, or other material. It will be understood that other types of lock mechanisms may be used to accomplish the herein-described purposes.

Figure 7:
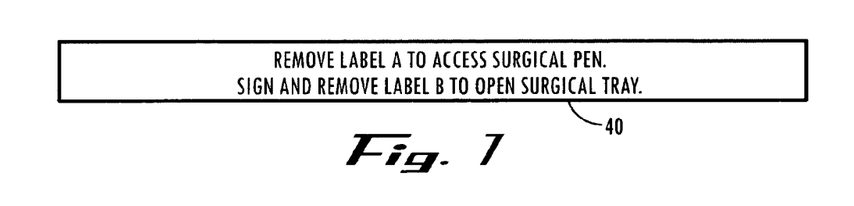
FIG. 7 is a plan view of an instructions label of FIG. 3.
Figure 8:
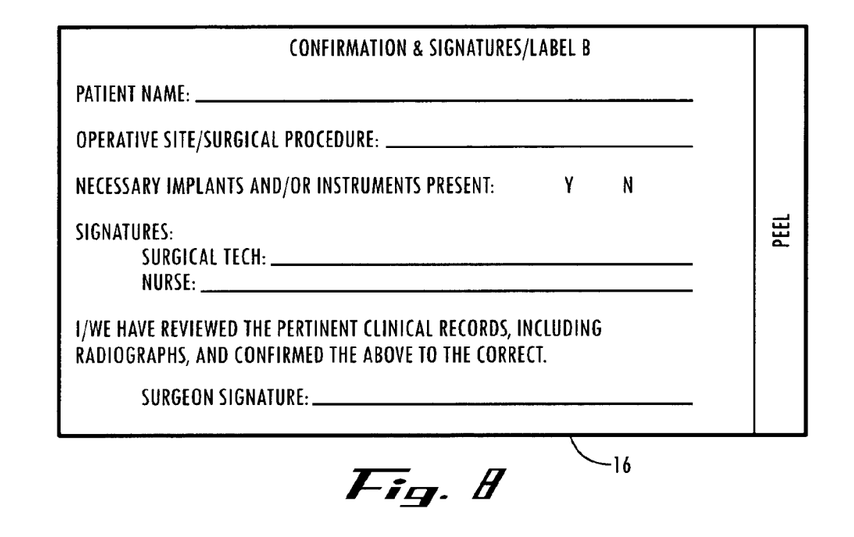
FIG. 8 is a plan view of the confirmation/signature label of FIG. 3.
Figure 9:
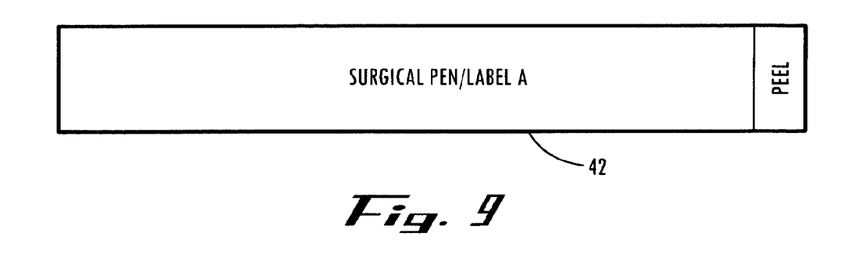
FIG. 9 is a plan view of a surgical pen-covering label of FIG. 3.

Referring additionally to FIGS. 7-9, the confirmation and signature label 16 is removable and covers the lock member 24 so it cannot be accessed to unlock the container 12 until the label is removed. In a typical commercial embodiment shown in FIG. 8, the confirmation and signature label 16 has a front side that can be written upon and that includes a checklist to be filled out by the surgical technician and fields where surgical team members sign after confirming that the information entered in the checklist is correct. For example, the checklist preferably provides for confirming the correctness of the patient name, the type/name of the surgical procedure, the laterality of the incision (left, right, or midline), and the laterality of the pathology (left, right, or midline), and for confirming that the proper instrumentation and any surgical implants are present and accounted for. It will be understood that the confirmation and signature label 16 may be customized for the same or other surgical uses, and thus is not limited to the specific representation depicted herein. Thus, in alternative embodiments, the checklist may call for the same surgery-related information of the depicted embodiment, only some of this information, or additional information. Preferably, the confirmation and signature label 16 is adhesive-backed and has a pull tab so that it can be easily removed from the container 12 and, if desired, placed in the medical record (the patient's record/chart/file) after it has been signed and removed.

In addition, the container 12 preferably has instructions for use prominently displayed on it. For example, in the depicted embodiment the instructions are marked on an adhesive-backed label 40 that is applied to the container top 20. Alternatively, the instructions may be printed or otherwise marked directly on the container 12 or elsewhere, or they may be omitted.

Figure 10:
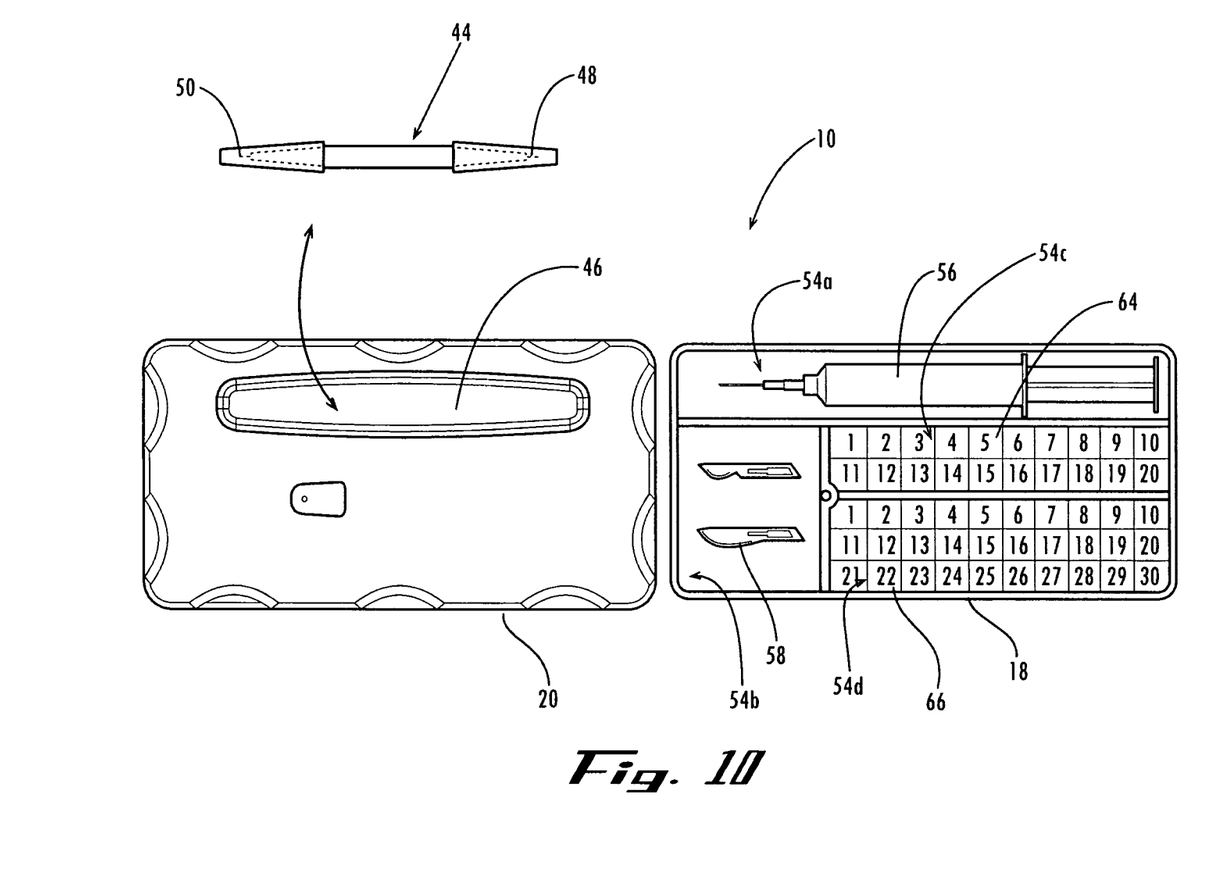
FIG. 10 is a plan view of the container of FIG. 1, ready for use, showing compartments holding a local anesthetic-loaded syringe and surgical blades for use in the surgery, and empty compartments for used suture and syringe needles.

Referring additionally to FIG. 10, the container 12 preferably has an adhesive-backed label 42 applied to the container top 20 to cover and hold a pen 44 within a recess 46 firmed in the container top 20. The pen 44 preferably has two marking tips 48 and 50 at opposing ends. A writing tip 48 is similar to a conventional ink pen for filling in and signing the confirmation and signature label 16. And a surgical tip 50 is similar to a conventional surgical pen with indelible ink for preoperatively marking the surgical site on the patient's body, and optionally for the signature of the surgeon. In alternative embodiments, the pen 44 may be removably attached to the container 12 by hook-and-loop fasteners or other conventional attachment structures, the pen 44 may be a conventional one-tipped ink or surgical pen, or it may be omitted. In addition, a small measuring ruler may be included in the recess 46 or provided (e.g., etched, printed, or otherwise applied), on the container, for example, at location 52.

The bottom 18 of the container 12 preferably includes a number of internal compartments (collectively referred to as the compartments 54) defined by the internal divider walls 38. The size, shape, and configuration of the compartments 54 are selected for the surgical implements desired to be held in the container 12, and as such may be customized depending on the surgery and the surgeon. In the depicted embodiment, the container 12 has a first compartment 54a that is pre-loaded with a syringe 56 containing a local anesthetic such as lidocaine, and a second compartment 54b that is pre-loaded with one or more surgical blades 58 such as Number 10 and 15 scalpels. It will be understood that the container 12 may be provided with both the syringe 56 and the blades 58, with only one of these, and/or with other surgical implements such as packets of surgical needles. In alternative embodiments, the compartments are sized, shaped, and configured for including other types of blades, handles for the blades, disposable single-unit scalpels, a syringe with another local anesthetic, arthroscopic probes, and/or other surgical implements needed to start the case. In addition, the second compartment 54b for the blades 58 may have a sheet of foam lining.

Figure 11:
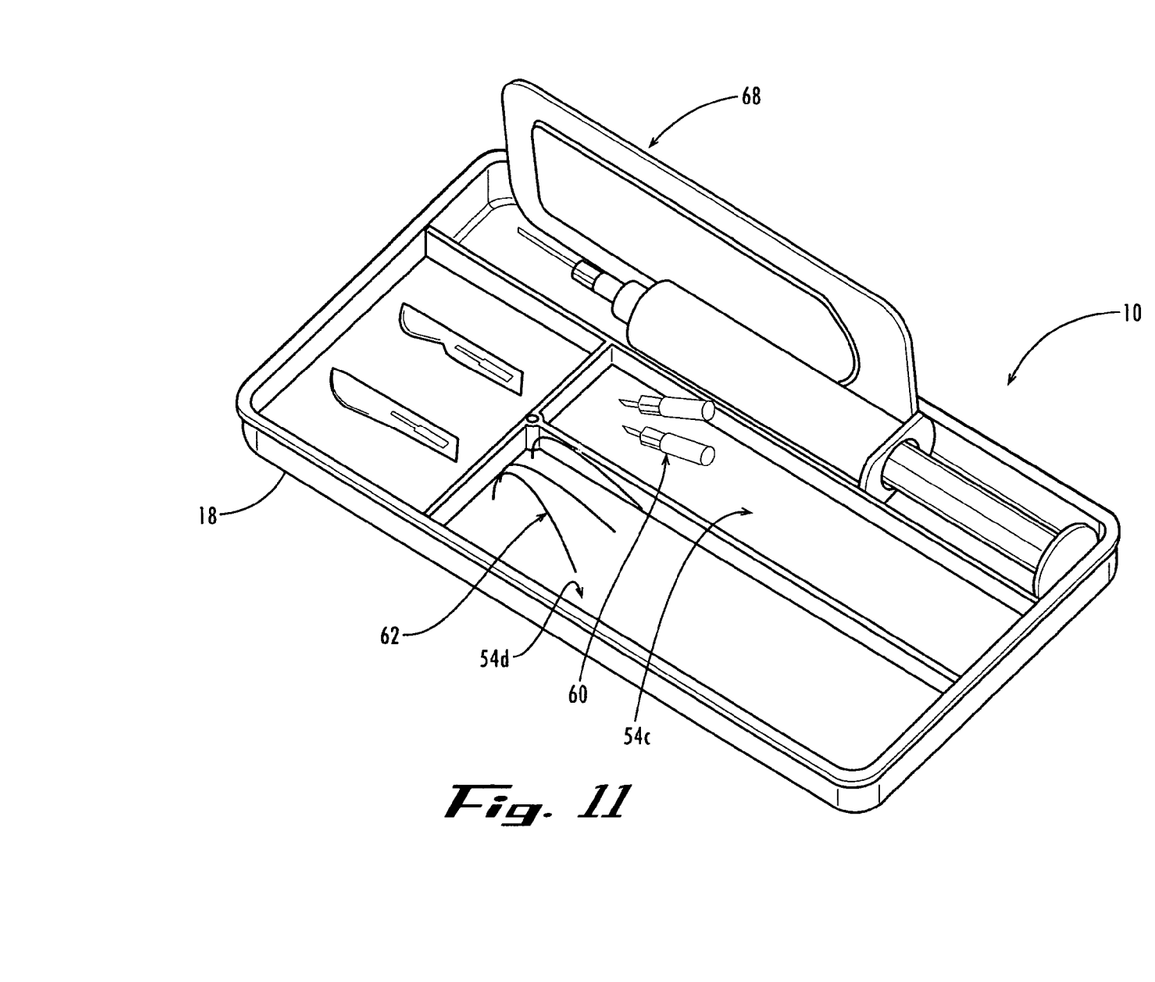
FIG. 11 is a perspective view of the container bottom of FIG. 10 in use, showing the used surgical suture and syringe needles stored in their dedicated compartments.

Referring additionally to FIG. 11, the depicted container 12 has a third compartment 54c and a fourth compartment 54d that are sized, shaped, and configured for storing used syringe and suture needles 60 and 62 after they have been used in the surgery. The compartments 54c and 54d are preferably each lined with an attachment sheet 64 and 66 that holds the used needles in place and that has numbered spaces for ease in counting the used needles. For example, the attachment sheet 64 and 66 may be made of a foam and/or magnetic material. In addition, the first compartment 54a can be used for miscellaneous purposes such as holding unused suture packages 68 so they are readily accessible as needed during the surgery. Thus, it will be noted that the container bottom 18 of FIG. 10 is shown just opened and ready for use, and the container bottom 18 of FIG. 11 is shown in the midst of use during the surgery.

A method of using the system 10 to prevent wrong-site surgeries will now be described. The container 12 is provided in the closed, locked position of FIGS. 1-3, preloaded with one or more surgical implements needed to start the surgery. The confirmation and signature label 16 prevents accessing the lock member 24, so the surgical team must deal with the label before it can unlock and open the container 12 to start the surgery. This effectively forces a pause or "time out" before the surgery can commence, thereby prompting the preoperative assessment. At this time, the surgical technician who is starting the case fills out the checklist on the label 16. For example, when using the confirmation and signature label 16 of FIG. 8, the surgical technician checks for the correct patient being present, the correct type/name of the surgical procedure, the correct laterality of the incision (left, right, or midline), the correct laterality of the pathology (left, right, or midline), and the presence of the proper instrumentation and/or needed surgical implants. The attending surgeon then confirms all the information written on the confirmation and signature label 16 by the surgical technician, and signs his name to indicate that he/she has personally reviewed and confirmed the information to be correct. Then the surgeon (or the technician) removes the confirmation and signature label 16 from the container 12, removes the lock member 24 (or otherwise actuates the lock mechanism to unlock the container), and opens the container 12 (see FIG. 4) to access the surgical implements in the container. The removed confirmation and signature label 16 can be placed in the medical record to document that the "time out" and confirmation was performed. At this point, the surgery start time is recorded, and surgery is considered started.

The individual hospital's operating room policy preferably requires the operating/attending surgeon to open the box him/herself, and/or to sign his/her name prior to making incision. In this way, the system 10 forces the surgical team to pause, at the same time in every case (namely, just prior to incision), to ensure that the correct surgery is being done, on the correct side, and to the correct patient, and that all needed surgical instrumentation or implants are available. It will be understood that other surgical systems that include a container for surgical implements and a confirmation and/or signature label that is positioned to block or impede opening of the container to force a pause just before the start of a surgery, but not specifically described herein, may be used with the system to accomplish the functionality described herein. It should also be noted that the system 10 is not meant to replace current pre-operative measures to prevent wrong-site surgery (i.e., all of JHACO's advice/recommendations), though it could, but rather it is designed to supplement those measures by providing a last chance to prevent wrong-site surgery by forcing the pause just before the incision.

The uniqueness of the system 10 provides additional safety features. One of these safety features relates to the "neutral zone," which is generally considered to be the area between the surgeon and the surgical technician, where the surgeon's hands and the surgical technician's hands are supposed to never meet. But in practice, this is a general and undefined area, and it can expand, shrink, and shift as the surgeon and technician lean over, turn slightly one side, and/or shift their weight during the course of the surgery. Because of this, and because of the focus on the patient and the surgical procedure, occasionally the surgeon and technician stick each other when passing sharp instruments back and forth.

Figure 12:
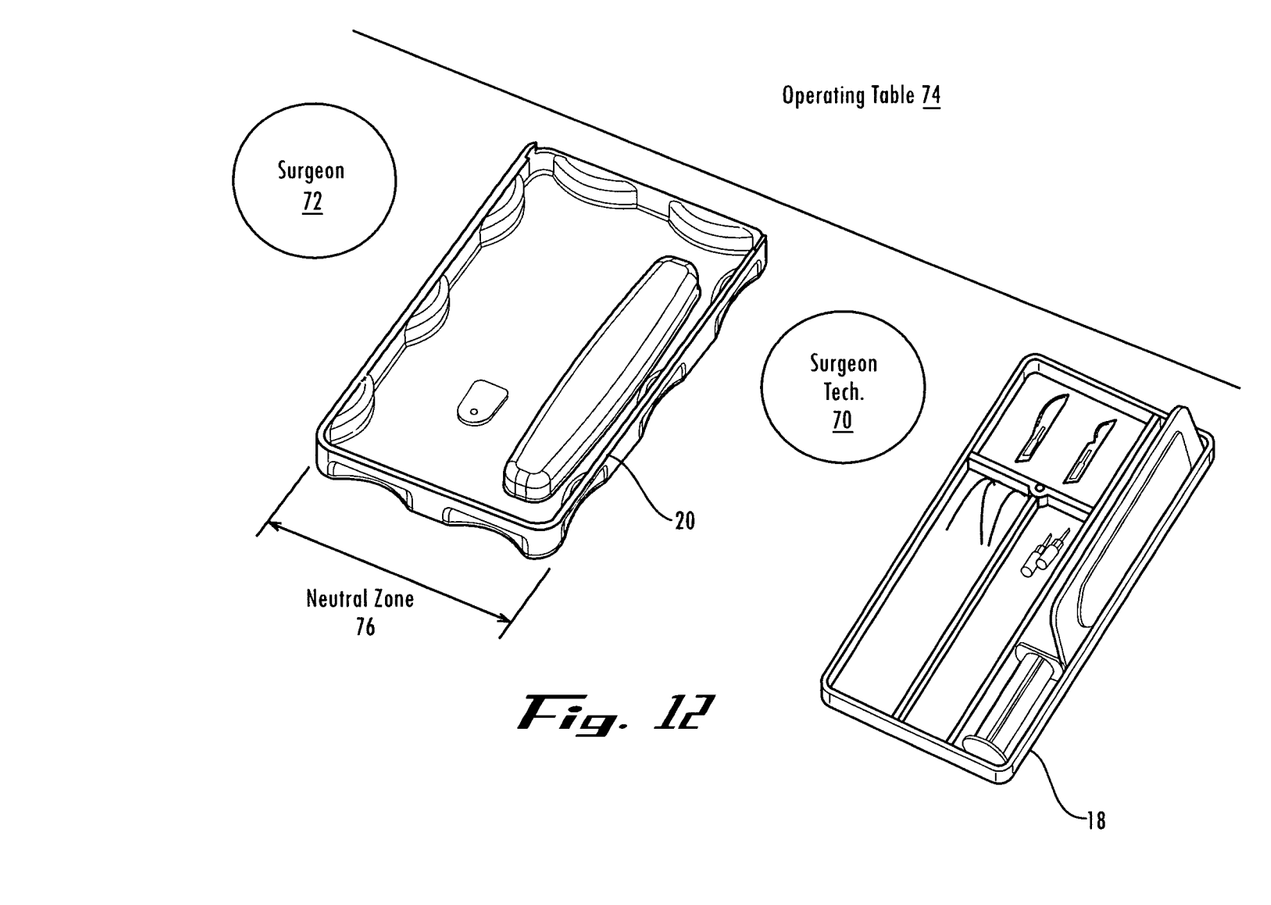
FIG. 12 is a schematic diagram of the container FIG. 10 in use, showing the container bottom holding the surgical sharps and the container top inverted and defining a neutral zone between the surgeon and the surgical technician.

Referring additionally to FIG. 12, after the container 12 has been opened to start the surgery, the container top 20 may be inverted and placed on a cart or other horizontal surface between the surgical technician 70 and the surgeon 72 as they face the operating table 74. As described above, the top surface of the container top 20 and the bottom surface of the container bottom 20 preferably have gripping features so that they do not slip and move during the surgery. In this position, the container top 20 defines a clearly demarcated, lateral neutral zone 76 where hands are not allowed to meet. When the surgeon 72 is done with a sharp instrument, he can simply place it in the neutral zone, that is, in the upside-down container top 20. The surgical technician 70 can likewise add or remove sharp instruments to or from the inverted container top 20. By the surgeon 72 and the surgical technician 70 never actually handing each other sharp instruments, but instead having a clearly defined neutral zone 76 for indirectly passing sharps to each other, the incidence of needle sticks can be reduced.

Furthermore, the container bottom 18 may be placed on a cart or other horizontal surface beside the surgical technician 70 (e.g., on the opposite side of the container top 20) or elsewhere in a position that is convenient for the technician. With the container bottom 18 accessible to the technician 70, he/she can use the container bottom during the surgical case to store all the used sharps (e.g., scalpels, needles), as shown in FIG. 11, similarly to how the technician would normally use a conventional sharps box or needle holder or counter. And the container 12 or at least its top 20 may be red in color, similar to a conventional sharps box, to help minimize the likelihood of needle sticks. Alternatively, another color such as purple or opaque may be used.

Moreover, at the end of the case, all the sharps used during the surgery can be put in the container 12, and the container can be closed and safely disposed of. The detents or other snapping structures of the container 12 hold the container closed. In addition, the lock mechanism 14 may be provided with detents or other snapping structures so that the lock member can be reinserted to secure the container 12 closed. This way, all of the surgical sharps used during the case can be safely disposed of as a single unit.

Figure 13:
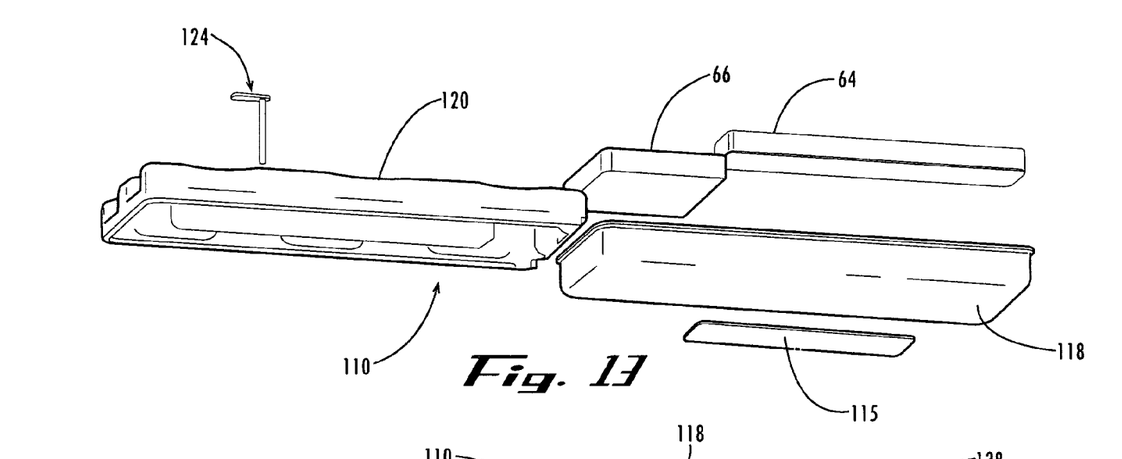
FIG. 13 is an exploded perspective view of a container for surgical sharps according to a second example embodiment.
Figure 14:
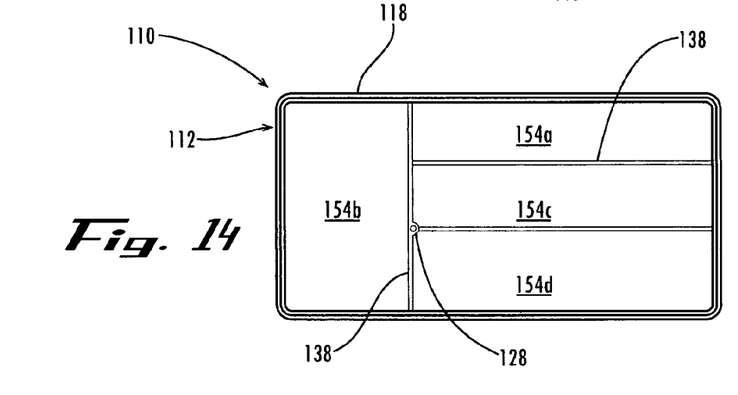
FIG. 14 is a plan view of the bottom of the container of FIG. 13.

Turning now to FIGS. 13 and 14, there is illustrated a surgical system 110 according to a second example embodiment of the present invention. Similarly to the system 10 of the first example embodiment, the system 110 includes a container 112 with a bottom 118 and a top 120, a lock mechanism having a lock member 124 that is received in alignable first opening and second opening 128, and a number of divider walls 138 forming compartments 154 for the surgical implements. In this embodiment, however, compartment 154b extends the all the way across the container bottom 120, and compartments 154a, 154c, and 154d each have the same length. In addition, the foam sheet inserts 64 and 66 for the compartments are configured for the different arrangement of the compartments.

Figure 15:
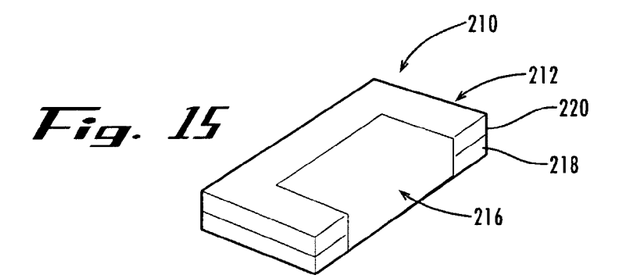
FIG. 15 is a perspective view of a container for surgical sharps according to a third example embodiment, showing the container in a closed and locked position.

Turning now to FIG. 15, there is illustrated a surgical system 210 according to a third example embodiment of the present invention. The system 210 is similar to that of the above-described embodiments, having a container 212 with a bottom 218 and a top 220 and a confirmation and signature label 216. In this embodiment, however, the label 216 is positioned extending across the bottom 218 and top 220 of the container 212 to hold it closed. In this way, the label 216 also functions as the lock mechanism, so a separate lock mechanism is not included. In use, after the label 216 is filled out, signed, and removed from the container 212, the container can be opened to start the case without additionally having to remove a separate lock member.

Figure 16:
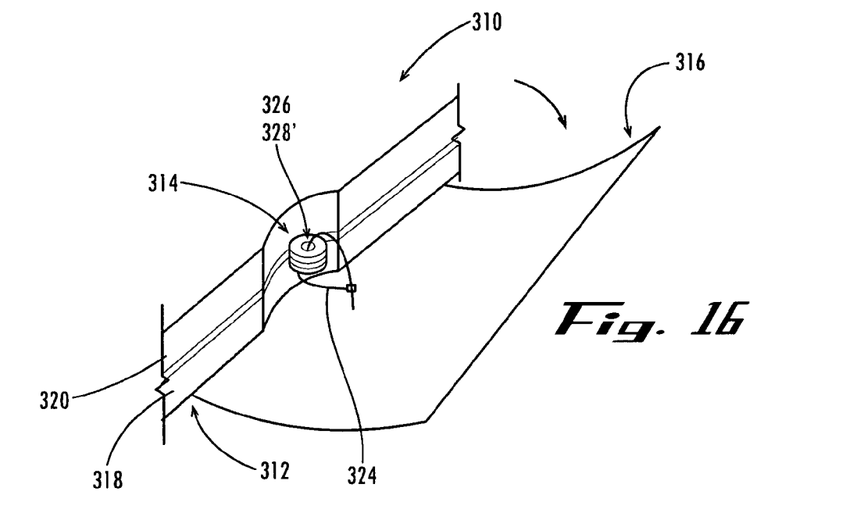
FIG. 16 is a perspective detail view of a container for surgical sharps according to a fourth example embodiment, showing a label being removed to expose a lock.

Turning now to FIG. 16, there is illustrated a surgical system 310 according to a fourth example embodiment of the present invention. The system 310 is similar to that of the first embodiment, having a container 312 with a bottom 318 and a top 320, and a lock mechanism with a lock member 324 received in two alignable lock openings 326 and 328. In this embodiment, however, the lock member is a plastic tie wrap or a twisty tie, and the alignable lock openings 326 and 328 are defined in tabs extending from the exterior of the container. In addition, the system 310 may include a spare tie 324 for relocking the container 312 after use for safe disposal. In an alternative embodiment, the lock mechanism is provided by a conventional slide-lock or snap-lock mechanism similar to that of commercially available surgical sharps boxes.

Figure 17:
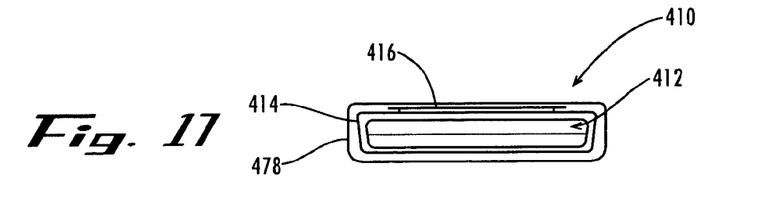
FIG. 17 is a side view of a container for surgical sharps according to a fifth example embodiment, showing a label positioned on a sterile inner wrapping enclosed by an outer wrapping.

Turning now to FIG. 17, there is illustrated a surgical system 410 according to a fifth example embodiment of the present invention. The system 410 is similar to that of the second embodiment, having a container 412 for surgical implements and a confirmation and/or signature label 416 for use and removal just prior to starting the surgery. In this embodiment, however, the lock mechanism is provided by a wrapper 414 with the label 416 on it. The wrapper 414 is preferably made of a clear plastic material and has a circumferential opener strip 415a with a pull tab 415b formed into it, similar to the wrapper, opener strip, and red pull tab on some conventional compact disc cases. The label 416 is preferably positioned on the wrapper 414 over the pull tab 415 so that when the label is peeled off, the pull tab 415b is pulled and the opener strip 415a is pulled to partially open the wrapper. The label 416 can be sized and shaped so that it wraps all the way, or most of the way, around the container 412, so that in order to remove the wrapper 414 the label must first be removed, thereby prompting the pause for the pre-operative assessment.

Figure 18:
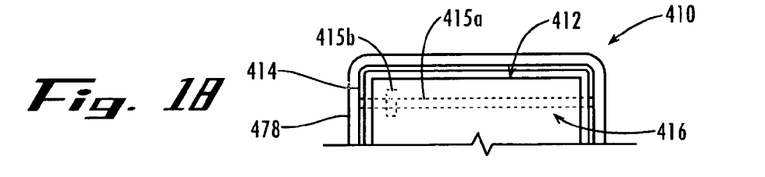
FIG. 18 is a plan detail view of the container of FIG. 17, showing an opener strip and pull tab of the sterile inner wrapper.

In the embodiments described herein, all of these components are sterilized so that the surgeon can sign the label at the operating table immediately prior to starting the surgery. To maintain the wrapper in sterile condition, a removable outer wrapper 478 is preferably provided that encloses the sterile components, as shown in FIGS. 17 and 18.

In other example embodiments, the system is provided with a container for surgical implements and a confirmation and/or signature label removably attached to the container, but without a lock mechanism for the container or with a lock mechanism that is not covered by the label. Instead, the label is positioned directly or indirectly on the container to merely impede opening the container, that is, the label is in a prominent position so that it is not easily overlooked and it thereby prompts the surgical team to conduct the pre-operative assessment. Such embodiments are provided by the first example embodiment modified without the lock mechanism, and the fourth example embodiment modified with the label on the container top only.

In still other alternative embodiments, the system includes a container with a scalpel (or other surgical implement) in it, with another way of forcing a pause without filling out a label. For example, the system can include a lock mechanism for the container that by itself forces the pause. The lock can be a small combination lock, with a combination that only the circulating nurse knows. The doctor and scrub tech confirm that they have the right patient and the right operation, and relay that information to the circulating nurse, who then confirms the information and gives them the code to open up the combination lock.

Accordingly, the present invention provides a number of advantages. In particular, the system and method of the invention insure a final confirmation of the correct patient, procedure, site, and as applicable, implants or instrumentation, is performed thoroughly and consistently, immediately prior to allowing incision to be made. The marking of the surgical site, the required use and removal of the confirmation checklist before accessing the surgical blades needed to start the surgery, and the resulting open communication between the patient, the surgeon, and the operating team, all contribute to reducing wrong-site medical errors. In addition, the surgical container provided by the invention can be used as a needle box for sharps disposal at the end of the case, and as a neutral zone during the case to decrease the incidence of needle sticks or lacerations from the surgeon and the surgical technician handing each other sharp instruments such as scalpels or needles. Furthermore, use of the invention can actually be extended to other areas of the hospital where an incision might be made, such as in the interventional radiology suite, the intensive care unit, or the emergency room.

It is to be understood that this invention is not limited to the specific devices, methods, conditions, or parameters described and/or shown herein, and that the terminology used herein is for the purpose of describing particular embodiments by way of example only. Thus, the terminology is intended to be broadly construed and is not intended to be limiting of the claimed invention. For example, as used in the specification including the appended claims, the singular forms "a," "an," and "the" include the plural, the term "or" means "and/or," and reference to a particular numerical value includes at least that particular value, unless the context clearly dictates otherwise. In addition, any methods described herein are not intended to be limited to the sequence of steps described but can be carried out in other sequences, unless expressly stated otherwise herein.

While the invention has been described with reference to an example embodiment, it will be understood by those skilled in the art that a variety of modifications, additions and deletions are within the scope of the invention, as defined by the following claims.

What is claimed is:

1. A method of preventing a wrong-site error during surgery, comprising:

accessing a container having a top portion containing a first lock opening sized and shaped to receive a locking pin and a bottom portion containing a second lock opening sized and shaped to receive a locking pin, said bottom portion adapted to slidably engage said top portion whereby said top portion and said bottom portion are movable between a closed position and an open position, each said lock opening positioned within said top or bottom portion to form an overlapping orientation to receive a locking pin when in the closed position, the container defining one or more internal compartments; one or more surgical implements positioned within the one or more compartments, wherein the surgical implements are needed when beginning the surgical procedure; a lock mechanism that secures the container in the closed position, the lock mechanism comprising a locking pin having at least one portion for linearly engaging said first and second openings when said container is in the closed position; and a removable label including a checklist for confirming surgery-related information and one or more fields for signatures, said label positioned in front of the locking pin to prevent or impede access to at least a portion of the locking pin without first removing the label;

verifying a correct surgical site and filling in the surgical-site information input field of the label with the surgical-site information to conduct a pre-surgery assessment confirming the correct surgical site;

removing the label from the container and saving it as a medical record for later documentation that the pre-surgery assessment confirming the correct surgical site was in fact conducted;

opening the container and removing the at least one surgical implement; and using the at least one surgical implement at the outset of the surgery, wherein the pre-surgery assessment confirming the correct surgical site is timely conducted before opening the container, removing the at least one surgical implement, and starting the surgery with the at least one surgical implement, and wherein timely conducting the pre-surgery assessment is prompted by the label being positioned to prevent or at least impede opening the container, and wherein the initial position, input field, and removal of the label effectively accomplish the dual purposes of first forcing the prompt for the pre-surgery assessment and then second documenting that the pre-surgery assessment in fact was conducted.

2. The method of claim 1, wherein
the step of removing the label from the container comprises removing the label from its initial position blocking access to the lock mechanism; and the step of opening the container comprises accessing and operating the lock mechanism to open the container.

3. The method of claim 1, wherein the container top is removed to open the container, and further comprising:

positioning the removed container top between a surgeon and a surgical team member to define a neutral zone where hands are not to meet; and exchanging surgical sharps between the surgeon and the surgical team member without sticking each other, wherein the surgeon places selected ones of the surgical sharps within the container top for the surgical team member to then pick up, and vice versa.

4. The method of claim 1, wherein the container bottom includes at least one compartment that holds the at least one surgical implement and one or more dedicated compartments for surgical needles, and further comprising:

removing the top and the bottom from each other; positioning the removed container bottom beside a surgical team member; and after the surgical needles have been used in the surgery, storing the used surgical needles in the dedicated compartments in the container bottom.

5. The method of claim 3, wherein the container bottom includes at least one compartment that holds the at least one surgical implement and including one or more dedicated compartments for surgical needles, and further comprising:

removing the top and the bottom from each other; positioning the removed container bottom beside a surgical team member; after the surgical needles have been used in the surgery, storing the used surgical needles in the dedicated compartments in the container bottom; replacing the top on the container to close the container; and disposing of the container with the used sharps safely inside.

6. The method of claim 1, wherein the step of saving the removed label as a medical record comprises placing the removed label in a corresponding patient chart.

7. The method of claim 3, wherein the surgeon and the surgical team member are both positioned on one side of an operating table, and wherein the step of positioning the removed container top between the surgeon and the surgical team member includes positioning the removed container top on the side of the operating table with the surgeon and the surgical team member.

8. The method of claim 5, wherein the step of positioning the removed container bottom beside a surgical team member includes positioning the removed container bottom on an opposite side of the surgical team member from the container top.

9. The method of claim 1, wherein the label includes at least one field for inputting a surgical team member signature, and further comprising the step of filling in the signature field of the label with the surgical team member signature to conduct the pre-surgery assessment confirming a correct surgical site.

10. The method of claim 1, wherein the step of removing the label from the container comprises removing the label from the container and saving the label intact as the medical record.

11. The method of claim 1, wherein the one or more surgical implements comprise a syringe loaded with a local anesthetic, at least one surgical blade, or both.

12. The method of claim 1, wherein the label in its initial position removably attached to the container extends across and is attached to first and second portions of the container to function as a lock mechanism retaining the container closed.

13. The method of claim 2, wherein said locking mechanism includes a tie member.

14. A method of preventing a wrong-site error during surgery, comprising:

accessing a container having a top portion containing a first lock opening sized and shaped to receive a locking pin and a bottom portion containing a second lock opening sized and shaped to receive a locking pin, said bottom portion adapted to slidably engage said top portion whereby said top portion and said bottom portion are movable between a closed position and an open position, each said lock opening positioned within said top or bottom portion to form an overlapping orientation to receive a locking pin when in the closed position, the container defining one or more internal compartments; one or more surgical implements positioned within the one or more compartments, wherein the surgical implements are needed when beginning the surgical procedure; a lock mechanism that secures the container in the closed position, the lock mechanism comprising a locking pin having at least one portion for linearly engaging said first and second openings when said container is in the closed position; and a removable label including a checklist for confirming surgery-related information and one or more fields for signatures, said label positioned in front of the locking pin to prevent or impede access to at least a portion of the locking pin without first removing the label;

verifying a correct surgical site, filling in the surgical-site information input field of the label with the surgical-site information, and filling in the signature input field of the label with the surgical team member signature, to conduct a pre-surgery assessment confirming the correct surgical site;

removing the label from the container and saving it as a medical record for later documentation that the pre-surgery assessment confirming the correct surgical site was in fact conducted;

opening the container and removing the at least one surgical implement;

using the at least one surgical implement at the outset of the surgery;

after the at least one surgical implement has been used in the surgery, storing the used at least one surgical implement in the container;

closing the container; and disposing of the closed container with the used at least one surgical implement safely inside, wherein the pre-surgery assessment confirming the correct surgical site is timely conducted before opening the container, removing the at least one surgical implement, and starting the surgery with the at least one surgical implement, wherein timely conducting the presurgery assessment is prompted by the label being positioned to prevent or at least impede opening the container, and wherein the initial position, input fields, and removal of the label effectively accomplish the dual purposes of first forcing the prompt for the pre-surgery assessment and then second documenting that the pre-surgery assessment in fact was conducted.

15. The method of claim 14, wherein the container top is removed to open the container, and further comprising:

positioning the removed container top between a surgeon and a surgical team member to define a neutral zone where hands are not to meet; and exchanging surgical sharps between the surgeon and the surgical team member without sticking each other, wherein the surgeon places selected ones of the surgical sharps within the container top for the surgical team member to then pick up, and vice versa.

16. The method of claim 15, wherein the surgeon and the surgical team member are both positioned on one side of an operating table, and wherein the step of positioning the removed container top between the surgeon and the surgical team member includes positioning the removed container top on the side of the operating table with the surgeon and the surgical team member.

17. The method of claim 16, wherein the container bottom that couples to the top and from which the top is removed to open the container, further comprising positioning the removed container bottom beside a surgical team member on an opposite side of the surgical team member from the container top, wherein the step of storing the used at least one surgical implement in the container comprises storing the used the at least one surgical implement in the container bottom.

18. The method of claim 14, wherein the one or more surgical implements comprise a syringe loaded with a local anesthetic, at least one surgical blade, or both.

19. The method of claim 14, wherein the label in its initial position removably attached to the container extends across and is attached to said top and bottom portions of the container to function as a lock mechanism retaining the container closed.

20. The method of claim 14, wherein:
the step of removing the label from the container comprises removing the label from its initial position blocking access to the lock mechanism; and
the step of opening the container comprises accessing and operating the lock mechanism to open the container.

21. The method of claim 20, wherein locking mechanism includes a tie member.

22. A method of preventing a wrong-site error during surgery, comprising:
accessing a container having a top portion containing a first lock opening sized and shaped to receive a locking pin and a bottom portion containing a second lock opening sized and shaped to receive a locking pin, said bottom portion adapted to slidably engage said top portion whereby said top portion and said bottom portion are movable between a closed position and an open position, each said lock opening positioned within said top or bottom portion to form an overlapping orientation to receive a locking pin when in the closed position, the container defining one or more internal compartments; one or more surgical implements positioned within the one or more compartments, wherein the surgical implements are needed when beginning the surgical procedure; a lock mechanism that secures the container in the closed position, the lock mechanism comprising a locking pin having at least one portion for linearly engaging said first and second openings when said container is in the closed position; and a removable label including a checklist for confirming surgery-related information and one or more fields for signatures, said label positioned in front of the locking pin to prevent or impede access to at least a portion of the locking pin without first removing the label;
verifying a correct surgical site and filling in the surgical-site input information field of the label with the surgical-site information to conduct a pre-surgery assessment confirming the correct surgical site;
removing the label from the container and saving it as a medical record for later documentation that the pre-surgery assessment confirming the correct surgical site was in fact conducted;
opening the container and removing the at least one surgical implement; and using the at least one surgical implement at the outset of the surgery,
wherein the pre-surgery assessment confirming the correct surgical site is timely conducted before opening the container, removing the at least one surgical implement, and starting the surgery with the at least one surgical implement, wherein timely conducting the presurgery assessment is prompted by being confronted with the label including the surgical site information field, and
wherein the prompt is forced by the at least one surgical implement being required at the outset of the surgery and held within the container and by the label being positioned to prevent or at least impede opening the container so that the label must be confronted in order to remove the label from the container to open the container to access the at least one surgical implement to begin the surgery, and wherein the initial position, input field, and removal of the label effectively accomplish the dual purposes of first forcing the prompt for the pre-surgery assessment and then second documenting that the pre-surgery assessment in fact was conducted.

* * * * *